Figure 1:
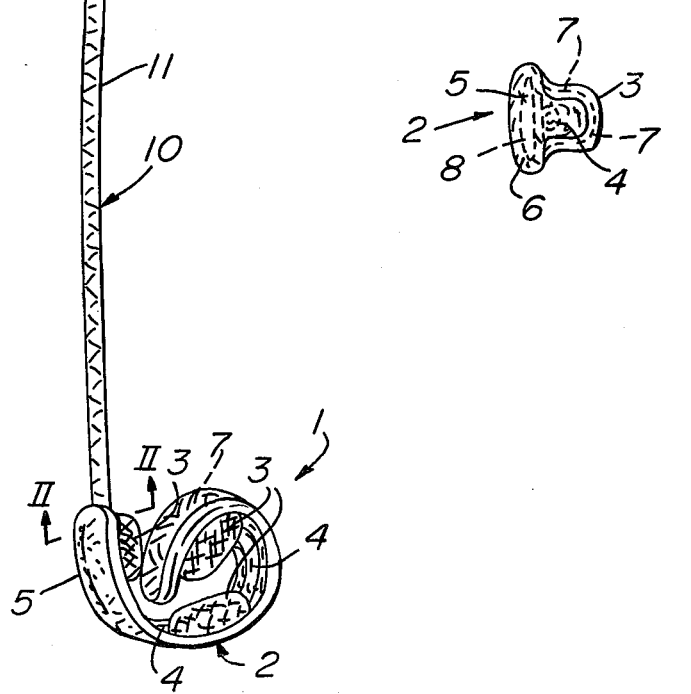

United States Patent [19]

Hakky

[11] 4,428,365
[45] Jan. 31, 1984

[54] ANTI-INCONTINENT PROSTHESES

[76] Inventor: Said I. Hakky, Sardoon, Bataween A² 15/14/1, Baghdad, Iraq

[21] Appl. No.: 353,719

[22] Filed: Mar. 1, 1982

[51] Int. Cl.³ .............................................. A61B 19/00
[52] U.S. Cl. ............................. 128/1 R; 128/DIG. 25
[58] Field of Search ............... 128/1 R, DIG. 25, 325, 128/346, 686, 344

[56] References Cited

U.S. PATENT DOCUMENTS

| 2,533,924 | 12/1950 | Foley | 128/DIG. 25 |
|---|---|---|---|
| 3,485,237 | 12/1969 | Bedford | 604/95 X |
| 3,610,235 | 10/1971 | Vagacs | 128/87 R |
| 3,744,063 | 7/1973 | McWhorter et al. | 128/1 R X |
| 3,866,611 | 2/1975 | Baumrucker | 128/DIG. 25 X |

OTHER PUBLICATIONS

Hargest, Thomas S. et al., "An Artificial Urethral Sphincter," Trans. Amer. Soc. Artif. Int. Organs, vol. XVII (1971), pp. 132–133.
Timm, Gerald W. et al., "Intermittent Occlusion System," IEEE Transactions on Biomedical Engineering, (Oct. 1970), p. 352.
Stanley, Theodore H. "Artificial Control of Fecal Incontinence," Surgery (Nov. 1970), vol. 68, No. 5, pp. 852–856.

Primary Examiner—William E. Kamm
Assistant Examiner—Christine A. Fukushima
Attorney, Agent, or Firm—Caesar, Rivise, Bernstein & Cohen, Ltd.

[57] ABSTRACT

An anti-incontinent prosthesis comprising a support member formable into at least one generally spiral turn for location about the corpus spongiosum. A plurality of inflatable chambers are disposed on the turn and connected to a pump means for applying fluid pressure to said chambers to constrict the urethra.

16 Claims, 2 Drawing Figures

U.S. Patent      Jan. 31, 1984      4,428,365

ANTI-INCONTINENT PROSTHESES

The present invention relates to an anti-incontinent prosthesis for controlling urinary incontinence. Such a prosthesis is implanted in the body of a patient suffering from incontinence, about the urethra, and enables the patient manually and voluntarily to control urination.

In humans, the act of urinating is controlled by two ring-like muscles acting on the corpus spongiosum, which contains the urethra or urinary duct, upstream and downstream of the prostate gland. The upstream muscle or internal sphincter is an involuntary muscular control whilst the downstream muscle or external sphincter provides the voluntary control, and it is loss of control of this latter muscle which results in incontinence.

It is known to control urinary incontinence by means of a fluid pressure operated prosthesis which is implanted adjacent the corpus spongiosum and which is pressurised by means of fluid pressure supplied from a manually actuated bulb in order to pinch or constrict the urethra and prohibit the flow of urine. The fluid pressure is delivered to the prosthesis via a non-return valve in the bulb outlet which can be manually distorted or deformed in order to release the pressure applied by the prosthesis and thereby open the urethra and permit urination, when desired. Prior prostheses of this type have not been satisfactory and have tended to be a health risk. They have generally been constructed so as to constrict the urethra about its entire periphery and this tends to jeopardise the blood supply to the urethra downstream of the prosthesis, thereby resulting in damage to the urinary organ. If the blood supply to the urethra is interfered with, a stricture or occlusion occurs.

An object of the present invention is to provide an anti-incontinent prosthesis of the fluid pressure operated type which reduces or avoids the risks associated with hitherto known prostheses of this type.

To this end, the present invention resides in an anti-incontinent prosthesis comprising a support member formable into at least one turn of generally spiral configuration, and a plurality of inflatable chambers disposed in spaced relation along the inside of the support member, when formed into said spiral turn, and connected in series by tubular portions of smaller cross section than the chambers, said series of chambers being connectable at one end to a device for applying fluid pressure to the chambers.

The support member is preferably a strip-like member which is bendable or deformable into the required configuration. For example, it may comprise a thin strip of bendable metal embedded or encased in a strip of silicone rubber or other synthetic material. Conveniently, the chambers are uniformly spaced along the inside face of the strip like support member, and each chamber is of part cylindrical shape and extends along the support member for only a relatively minor portion of its length. Similarly to the support member, the chambers and interconnecting tubular portions may be formed from silicone rubber or other synthetic material. A reinforcing net or mesh may be embedded in the walls of the chambers and interconnecting tubular portions so as substantially to prevent these parts from expanding when pressurised.

The device for applying fluid pressure to the inflatable chambers may comprise a flexible bulb containing pressure fluid and connected to one end of the series of chambers by a flexible tube, the bulb incorporating a non-return valve arranged to prevent fluid, discharged from the bulb into the series of chambers, from returning to the bulb. However, the valve is deformable so that it can be manually deformed or distorted so as to permit fluid return and depressurisation of the chambers.

The prosthesis of the invention is implanted in the body of a patient adjacent the external sphincter. It is disposed about the corpus spongiosum in a generally spiral configuration so that the inflatable chambers engage against the corpus spongiosum. The pressurising bulb is also implanted in a suitable position in the body. In the case of a male, it may be implanted in the dartos pouch of the scrotum and the tube connecting the bulb to the chambers is also suitably implanted so that there is no visible evidence of the implant. When the patient requires to prevent incontinence, it is a simple matter to squeeze the bulb so as to inflate the chambers of the prosthesis which, thereupon, press against the corpus spongiosum and constrict the urethra. Although the inflatable chambers are spaced apart, by reason of the spiral configuration of the prosthesis, they satisfactorily constrict the urethra to prohibit incontinence. By reason of their spacing, there is no continuous zone of pressure about the corpus spongiosum which would restrict the supply of blood to the urethra and thereby produce a stricture or occlusion. With the present invention, the blood can flow freely through the unpressurised zones of the corpus spongiosum adjacent the interconnecting tubular portions, even when the prosthesis is pressurised or inflated. When the patient desires to urinate, it is a simple matter for the patient to locate and deform the non-return valve so as to depressurise the inflated chambers and enable the urethra to open.

The fluid for inflating the chambers of the prosthesis is charged into the prosthesis, tube and bulb at atmospheric pressure and may be a gas or liquid. If a liquid is utilized, this should preferably be decanted to render it gas free before it is charged into the prosthesis. When the prosthesis is being implanted, the surgeon can readily test the amount of fluid pressure required to be applied to the chambers in order to adequately and comfortably constrict the urethra and prohibit incontinence and can charge the pressure fluid into the prosthesis, tube and bulb accordingly.

Figure 2:
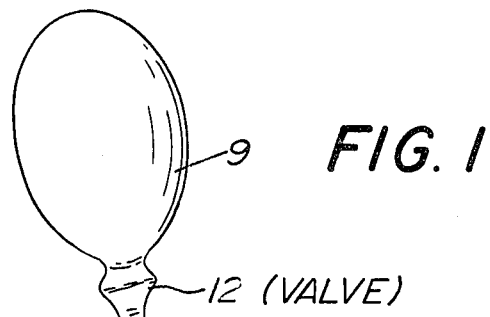

In order that the invention may be readily understood, reference will now be made to the accompanying drawings, in which:

FIG. 1 is an elevational view of the prosthesis and of the bulb for applying fluid pressure thereto, and FIG. 2 is a cross section on the line II II of FIG. 1.

Referring to the drawings, the prosthesis 1 comprises a strip like support member 2 formable into at least one turn of generally spiral or helical configuration as shown in FIG. 1. Three inflatable chambers 3 are disposed in uniformly spaced relation along the inside face of the spiral turn of the support member and are connected in series by tubular portions 4 of substantially smaller cross section than the chambers. The support member comprises a bendable metal strip embedded in a strip-like body 6 of silicone rubber which is significantly wider than the metal strip. Each chamber 3 is of less width than the strip-like body, is of part cylindrical shape as illustrated in FIG. 2, and extends along the strip-like support member for only a relatively minor proportion of its length. The tubular portions 4 connect opposite ends of the central chamber 3, to the chambers at opposite ends of the support member. The chambers and tubular portions are also formed from silicone rubber. A reinforcing net or mesh 7 of non-stretchable material, such as DACRON (DACRON being a trademark for a synthetic fiber made from the condensation of dimethyl terephthalate and ethylene glycol, and sold by E. I. duPont d.e. Nemours and Co. of Wilmington, Del.) mesh, is embedded in the walls of the chambers and tubular portions and body 6, so as securely to fasten the chambers and tubular portions to the body and substantially prevent them from expanding, when inflated. The reinforcing mesh may also include a flattened sleeve like portion 8 surrounding the bendable metal strip 5.

The inflatable chamber at one end of the support member is connected to a flexible bulb 9 by means of a flexible tube 10 joined to the outer end of the chamber. This tube 10 is reinforced by a spiral filament of rigid plastics material 11 which is embedded in the tube along the full length thereof. The bulb may be moulded from silicone rubber and incorporates a non-return valve 12 at its outlet. This valve may be of a conventional construction and is not shown in detail. It permits liquid to be discharged from the bulb, when the bulb is pinched, to pressurise both the chambers 3. The valve has a deformable valve housing which can be deformed or distorted by manual pressure so as to open the valve, when it is desired to permit the pressurised fluid to return to the bulb in order to depressurise the chambers.

The prosthesis 1 is implanted in a patient suffering from urinary incontinence adjacent the external sphincter. As it is implanted, the supporting member 2 is bent about the corpus spongiosum of the patient to form at least one turn of generally spiral configuration with the inflatable chambers 3 engaging the external surface of the corpus spongiosum at spaced positions along a generally spiral path. The bendable metal strip 5 retains the silicone rubber parts of the prosthesis in the position in which they are set by the surgeon. The bulb and tube 9, 10 are also implanted in the patient. In the case of a male, the bulb 9 is implanted in the patient's dartos pouch. In order to prohibit incontinence, the bulb 9 is manually squeezed by the patient so that the chambers 3 are inflated and press against the corpus spongiosum so as to constrict the urethra. When the patient desires to urinate, it is a simple matter to locate and manually deform the valve 12 so as to release the pressure in the chambers and open the urethra.

Whilst a particular embodiment has been described, it will be understood that modifications can be made without departing from the scope of the invention.

I claim:

1. A prosthesis for controlling urinary incontinence comprising support means including a portion in the form of at least one turn of a spiral, said portion including a wall of generally non-stretchable construction and arranged for disposition about the corpus spongiosum and urethra, plural inflatable chambers located at spaced locations along said portion and means for inflating said chambers with a fluid to constrict said urethra.

2. The prosthesis of claim 1 wherein said means for inflating comprises pump means.

3. The prosthesis of claim 2 additionally comprising valve means coupled to said pump means, said pump means being arranged to provide fluid to said chambers to inflate said chambers, said valve means being arranged to prevent said fluid from returning to said pump means until desired.

4. The prosthesis of claim 1 wherein said support means comprises a strip.

5. The prosthesis of claim 4 wherein said strip is formed of bendable material having a silicone rubber covering.

6. The prosthesis of claim 1 wherein said chambers are interconnected by passage means having a substantially smaller cross sectional area than said chambers.

7. The prosthesis of claim 1 wherein each of said chambers is of partial cylindrical shape.

8. The prosthesis of claim 7 wherein said chambers are interconnected by passage means having a substantially smaller cross sectional area than said chambers.

9. The prosthesis of claim 1 wherein each chamber is formed of a resilient material.

10. The prosthesis of claim 9 wherein said material is silicone rubber.

11. The prosthesis of claim 10 wherein each chamber is reinforced by non-stretchable reinforcing means.

12. The prosthesis of claim 11 wherein said reinforcing means is formed of a mesh.

13. The prosthesis of claim 12 wherein said mesh is formed of a synthetic fiber made by the condensation of dimethyl terephthalate and ethylene glycol.

14. The prosthesis of claim 13 wherein said chambers are interconnected by passage means having a substantially smaller cross sectional area than said chambers.

15. The prosthesis of claim 14 wherein each of said chambers is of partial cylindrical shape.

16. The prosthesis of claim 15 wherein said support means comprises a strip formed of bendable material having a silicone rubber covering.

* * * * *